United States Patent [19]

Cherksey

[11] Patent Number: 4,895,807
[45] Date of Patent: Jan. 23, 1990

[54] MEMBRANE CHANNEL PROTEIN AND RELATED THERAPEUTIC COMPOUNDS

[76] Inventor: Bruce D. Cherksey, 608 Garden St., Hoboken, N.J. 07030

[21] Appl. No.: 948,262

[22] Filed: Dec. 31, 1986

[51] Int. Cl.$^4$ ............... G01N 33/483; C07K 3/02; C07K 3/20; C07K 15/00
[52] U.S. Cl. .................................. 436/63; 435/7; 436/531; 530/350; 530/395; 530/400; 530/417; 530/813; 530/828; 530/835; 530/839; 530/841; 530/844
[58] Field of Search ............... 530/350, 400, 395, 417, 530/835, 839, 841, 844, 828, 813; 435/7; 436/63, 531

[56] References Cited

U.S. PATENT DOCUMENTS 4,362,737 12/1982 Shäfer et al. .................. 514/56 X

OTHER PUBLICATIONS

Dialog Record No. 07203578; Embase Abstract No. 88201968.
Dialog Record No. 0018692255; Biosis Abstract No. 86094730.
Dialog Record No. 0018649248; Biosis Abstract No. 86072616.
Dialog Record No. 0018587734; Biosis Abstract No. 86043968.

*Primary Examiner*—Barry S. Richman
*Assistant Examiner*—Jill Johnston
*Attorney, Agent, or Firm*—Lyon & Lyon

[57] ABSTRACT

A channel protein has a molecular weight of approximately 280 kD and is capable of affecting K$^+$ and Cl$^-$ membrane transport. Furosemide and quinine derivatives, and polysaccharide or monosaccharide gels incorporating such derivatives, are useful in treating membrane transport, cellular volume and cellular pressure disorders and in producing the channel protein. The channel protein is used in diagnostic assays and screening assays is described.

12 Claims, 1 Drawing Sheet

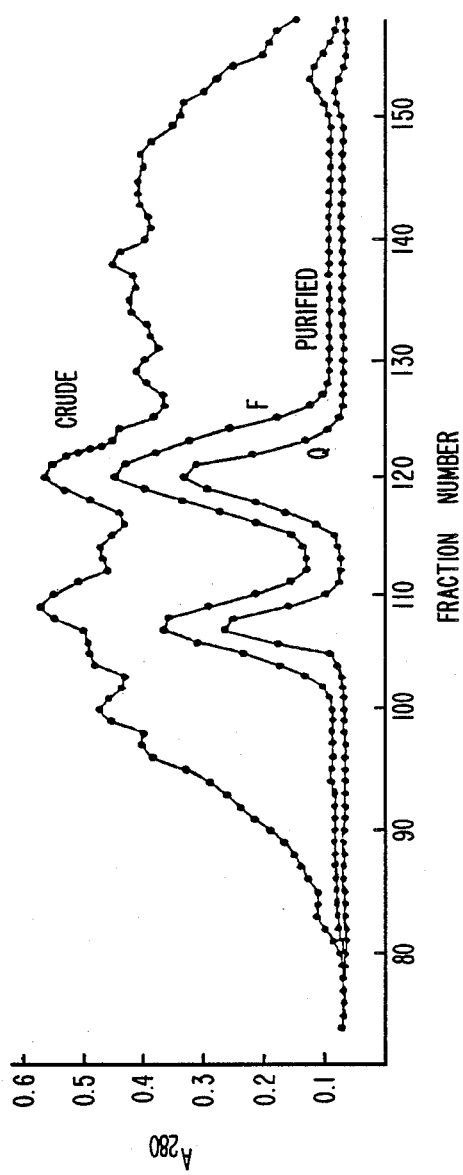

MEMBRANE CHANNEL PROTEIN AND RELATED THERAPEUTIC COMPOUNDS

BACKGROUND OF THE INVENTION

The ability to control transport of chemical species across cellular membranes is important from a therapeutic standpoint inasmuch as a number of disease conditions, including glaucoma and certain kidney and stomach disorders, are directly related to such transport. In addition, a better understanding of the mechanisms for such transport can be expected to yield improved therapeutic and diagnostic tools.

It is thought that transport of ions across membranes, as for example $K^+$ and $Cl^-$ ions, is controlled in part by membrane channel proteins which exist in certain membranes and which act to transport or "channel" ions across such membranes. Agents which selectively block ion transport have been described, as for example furosemide (an anion blocker, U.S. Pat. No. 3,058,882) and quinine (a cation blocker). Furosemide is widely thought to interact with a hypothetical sodium/potassium/dichloride "cotransporter" (as distinct from a channel protein), while quinine is thought to block $K^+$ channels. Only about six or so channel proteins have actually been isolated, and each of these is thought to transport only a single ionic species (e.g., $K^+$ or $Cl^-$, but not both).

The present invention involves, in part, a newly discovered channel protein responsible for membrane transport of both $K^+$ and/$Cl^-$ ions. It has been further discovered that quinine, furosemide and certain new furosemide derivatives are capable of binding to this $K^+/Cl^-$ channel protein, thereby blocking both $K^+$ and $Cl^-$ transport as controlled by that specific channel protein. By utilizing such channel protein binding compounds in affinity gels, it has been shown in investigations relating to the present invention to be possible to isolate and purify the channel protein. The channel protein and the binding compounds are useful in therapeutic control of membrane transport and in developing assays related to membrane control.

SUMMARY OF THE INVENTION

The present invention involves a newly-discovered membrane channel protein which has been found to be related to both $K^+$ and $Cl^-$ ion transport across cellular membranes. The channel protein has a molecular weight of approximately 280 to 300 kD, as determined for example by SDS-polyacrylamide gel electrophoresis, and has been found in a wide variety of cell samples. Discovery of this channel protein provides an avenue for regulating ion transport across membranes by utilizing transport blockers which bind to the protein. Such regulation may also be modulated by the use of $Ca^{++}$, pH or other media adjustments in in vivo or in vitro systems.

It has also been discovered that certain channel protein blocking compounds, in particular quinine, furosemide and certain furosemide derivatives, may be used to regulate the transport activity of the protein by virtue of their ability to bind to it. Such compounds would be useful in oral, ocular, topical or other administration media to correct membrane transport, cellular volume or cellular pressure disorders such as those associated with glaucoma, gastric ulcers, diuresis problems and the like. Preferred blocking compounds include Diels-Alder ketone adducts of furosemide.

The foregoing furosemide and quinine channel protein blocking compounds may also be covalently bonded to polysaccharide or monosaccharide (simple carbohydrate) support materials, such as those commonly used for gel affinity chromatography, to yield materials which are useful in isolating and purifying the channel protein. Such gel materials are also useful in their own right as therapeutic compounds capable of regulating membrane transport, cellular volume or cellular pressure disorders. The blocking compounds may also be bonded to other useful groups, such as radiolabels or fluorescence labels.

The channel protein is useful in developing diagnostic assays, as for example immunoassays and fluorescence assays, relating to membrane transport, cellular volume or cellular pressure disorders in appropriate membrane systems. It may also be used in in vitro screening assays to screen large numbers of test compounds for activity in modulating transport, volume and pressure controls in in vivo and in vitro systems.

Thus, in one respect, the present invention relates to a new and useful protein which has been shown to act as a channel for $K^+$ and $Cl^-$ ions in a variety of naturally-occurring cellular membranes. The protein is useful as an agent for developing diagnostic assays, as for example, immunoassays utilizing monoclonal or polyclonal antibodies, or fluorescence assays, which may be directed toward determining, in histopathological samples, the extent to which volume and pressure problems may result from abnormally high or abnormally low presence of the $K^+/Cl^-$ channel in appropriate membranes. In another aspect, the channel protein is useful as an agent for measuring in vitro the effectiveness of experimental compounds in displacing known blockers of the channel protein, thus furnishing a relatively inexpensive means for screening such compounds for therapeutic transport-modulation activity.

The present invention also provides methods for producing the channel protein and useful compositions related thereto. These methods involve the use of new and useful compositions which bind to and/or block the channel protein, including such compositions covalently bonded to modified polysaccharide or monosaccharide support materials derived from, for example, purified agarose, dextran, cellulose, or short-chain polysaccharides or monosaccharides such as glucose or dextrose. Such compositions, when bonded to a support structure, are useful in purifying the channel protein from membrane material. In addition, the compositions in their pure and/or saccharide-bound forms are useful in treating transport-related disorders such as ulcers, diuresis-related disorders, diarrhea and glaucoma.

Other uses for the invention described herein may also be readily recognized and practiced by persons skilled in the art.

BRIEF DESCRIPTION OF THE DRAWING

The FIGURE depicts the optical absorbance of eluted gel chromatography fractions containing crude (upper) and purified (F,Q) channel protein.

DETAILED DESCRIPTION

The diuretic and antihypertensive drug furosemide (5-aminosulfanoyl)-4-chloro-2-[(2-furanoylmethyl)amino]benzoic acid) is known to block anion transport across membranes, while the antimalarial, analgesic and antipyretic drug quinine (6'-methoxycinchonan-9-ol) is known to block cation transport. Derivatives of these drugs have been shown in gel affinity chromatography experiments relating to the present invention to be useful in purifying a membrane protein from the ventricular membrane of the choroid plexus, as well as from bovine kidney cortex, bovine brain cortex, bovine heart muscle, rabbit small intestinal baso-lateral membrane and murine Ehrlich ascites tumor cells. Surprisingly, both the furosemide and the quinine affinity gel purify the same protein of molecular weight of about 280 to 300 kD (as measured by SDS-polyacrylamide gel electrophoresis or gel filtration). The protein was not observed in human red blood cells or in apical membrane from small intestine or cornea. This protein has been shown to be a membranal "channel protein" which incorporates a $K^+$ as well as a $Cl^-$ channel, as ascertained from electrical measurements on protein inserted into planar lipid bilayers. Furthermore, the channel protein is unique in that it binds both furosemide and quinine, a property never observed in known channel proteins.

The furosemide gel used in purifying the present $K^+/Cl^-$ channel protein comprises a Diels-Alder ketone adduct of furosemide which has been covalently bonded to a modified polysaccharide or monosaccharide (simple carbohydrate) support. It is thought that such an adduct should be formed on the furan ring of furosemide inasmuch as the remainder of the molecule is believed to be important to the binding activity and pharmacological activity of furosemide. Other adducts may be used if they are capable of facilitating a covalent bond between the furosemide and the polysaccharide or monosaccharide support material while retaining the ability to bind to the channel protein. A methyl vinyl ketone adduct formed by the following reaction has been shown to be particularly useful in forming affinity gels for the $K^+/Cl^-$ channel protein:

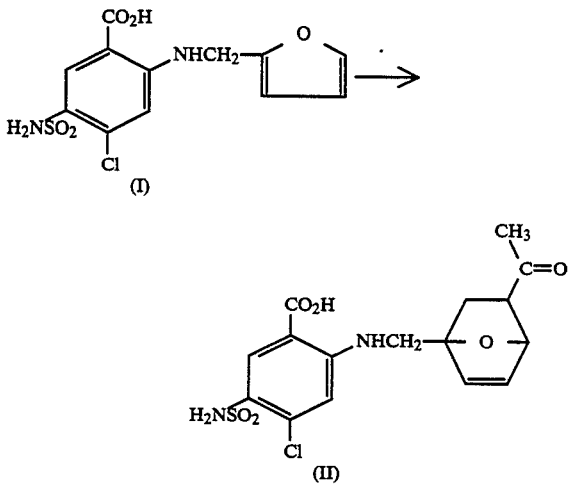

EXAMPLE I

Preparation of methyl vinyl ketone adduct of furosemide

One gram of furosemide (I, 2.3 mM) is gently refluxed in the dark under nitrogen using a large excess (50 ml) of methyl vinyl ketone as solvent. Five ml of diisopropylamine is added as catalyst and reflux is continued for several days, the color first turning red, then brown. It is believed to be highly important to the practice of the present invention to use a large amount of the diisopropylamine catalyst, a fact not suggested by any of the prior art. In addition, it is believed to be highly important to continue the reflux until a brown solution is achieved, which is also not suggested by the prior act. Thin layer chromatography on silica gel using a solvent mixture of ethyl acetate:acetic acid:ethanol 80:10:10 may be used to follow the conversion of furosemide (I) to its adduct (II) and the product may be isolated as early as TLC indicates that the reaction is essentially complete. The solvent is then removed by concentrating to dryness under vacuum and the residue is dissolved in a small volume of chloroform which is then evaporated to dryness several times to remove traces of methyl vinyl ketone. The product, which is an oil, is redissolved in a minimal volume of chloroform and diluted slowly with methanol to afford a pale solid. The solid may be further purified by crystallization from chloroform-methanol or instead, if desired, by chromatography, to give the Diels-Alder reaction product, namely the methyl vinyl ketone adduct of furosemide (II) in essentially pure form.

By virtue of its ability to bind to and block the transport activity of the channel protein, the above adduct and furosemide ketone adduct derivatives or other derivatives related to it may also be useful in directly treating disorders related to abnormal transport activity in membranes. For example, the materials are conceived to have useful diuretic activity when given orally and to be useful when applied topically for the prevention and treatment of glaucoma. In these uses, the materials may be formulated in vehicles standard for oral or ocular use and are given in amounts sufficient to affect aqueous transport but below amounts having toxic or irritating properties.

The above furosemide ketone adduct may also be bonded to a fluorescence label, such as fluoroscene isothiocyanate or rhodamine, by use of an alkylidine diamine spacer arm as discussed below with respect to gel preparation. The radio labeled ketone adduct may also be prepared. Such compounds may be used in assaying presence of the channel protein in cell samples or in quantitating displacement of the labeled compound from the channel protein by test compounds, as discussed below.

The furosemide gels used in purifying the $K^+/Cl^-$ channel protein may be formed by covalently bonding the above furosemide methyl vinyl ketone adduct, or analogous Diels-Alder ketone adducts, to a modified polysaccharide support, as, for example, a support derived from a purified agarose (e.g., Sepharose ® (Pharmacia)), from an α-linked dextran (e.g., Sephadex ® (Pharmacia)) or from cellulose. Short-chain polysaccharides, or monosaccharides, as for example glucose or dextrose, may also be used. Although such affinity purification compositions will be referred to herein as "furosemide gels," when the saccharide is short or is not cross-linked the composition may not in fact be a typical gel.

Preparation of such furosemide gels may be accomplished using CNBr by methods standard in the art. However, a preferred method involves the production in the polysaccharide of a variable number of aldehyde functions by partial oxidation of vicinal alcohols with periodic acid. The thus-modified polysaccharide is then treated with an alkylidine diamine ($H_2N(CH_2)_n NH_2$) where $n=2-8$, preferably $n=3-6$, and the methyl vinyl ketone adduct of furosemide is added. Diaminopropane (trimethylene diamine) is one particularly suitable alkylidine diamine. The Schiff bases produced from this mixture are then reduced with sodium borohydride or with sodium cyanoborohydride to produce the final stable product. The product is a furosemide gel formed by linkage of the furan ring of the furosemide compound to, for example, Sepharose ® CL-4B via a spacer arm diaminopropane.

EXAMPLE 2

Preparation of "furosemide gels"

Using procedures described in *Affinity Chromatography* by W. H. Scouten, John Wiley and Sons, 1981, pages 45–49, and in *Affinity Chromatography* edited by P. D. G. Dean, W. S. Johnson and F. A. Middle, IRL Press, 1985, gels may be produced from the methyl vinyl ketone adduct of furosemide (II) and various polysaccharide gels, such as Sepharose ®, Sephadex ® and cellulose. By way of illustrative example, 100 ml of agarose beads are washed with water and freed of interstitial water by suction filtration and are then added to 80 ml of water. To the suspension is added 20 ml of 1M sodium periodate. The suspension is shaken for 2–4 hours at room temperature in the dark. The thus oxidized agarose, for example Sepharose ®, is now ready for addition of an alkyl diamine spacer. It may be stored, if desired, for one to three days in the refrigerator in the dark prior to use.

The thus prepared oxidized agarose is added to 100 ml of an aqueous 2M solution of diaminopropane, pH 5.0. After 6–10 hours at room temperature, the pH is raised to 9 and the beads are reduced at 0–4 degrees C by the addition of 10 ml of 5M sodium borohydride or sodium cyanoborohydride over 12 hrs. Throughout the preparation of the gel, reaction is facilitated by gentle shaking. The beads are finally washed thoroughly with 1M sodium chloride to remove completely any traces of reducing reagent.

The thus produced agarose gel containing diaminopropane spacer is dried by suction filtration, washed with water, and added to 100 ml of water. To this suspension is added slowly a solution of the methyl vinyl ketone adduct of furosemide (II) in a small volume of water containing just sufficient 0.1M sodium hydroxide to dissolve the adduct. The pH is adjusted by addition of an equal volume of 0.1N acetic acid and the suspension is then shaken for several days at room temperature under nitrogen to form the Schiff base adduct of II. The pH is then raised to 9 and the Schiff base reduced by addition of sodium borohydride or sodium cyanoborohydride as described above. The thus produced "furosemide gel" is washed thoroughly with 1N saline and then with water and dried by suction filtration. If desired, it may be further dried to yield a dry powder by drying under vacuum at 30–60 degrees C. The thus produced gel or powder is useful as a reagent to isolate the purified $K^+/Cl^-$ channel. It is also useful when administered orally in producing diuresis, inhibiting gastric acid secretion and treating diarrhea. It is useful when applied topically in treating glaucoma.

In the above example, diaminopropane may be replaced by ethylene diamine, hexamethylene diamine, pentamethylene diamine and the like to afford the correspondingly modified "furosemide gels" in which the spacer link contains 2, 6, and 5 carbon atoms, respectively. Furthermore, agarose may be replaced by commercially available supports such as an alpha-linked dextran (e.g. Sephadex ®) or cellulose to afford the corresponding gels containing compound II. Similar gels may be formed using short-chain polysaccharides or monosaccharides such as glucose or dextrose using the above method or other methods standard in the art.

It has also been found that affinity gels formed from modified polysaccharide support materials and quinine are useful in purifying the $K^+/Cl^-$ channel protein. Such "quinine gels" comprise quinine covalently bonded to a 1,4-butanediol diglycidyl ether-modified polysaccharide support material, such as agarose (e.g. Sepharose ® 4B). The gels may be produced in a manner analogous to that described by Caron et al., *J. Biol. Chem*, Vol. 254, pp. 2923–2927 (1979), in the procedure titled "Preparation of Alprenolol Agarose Gel (p. 2926), by substituting an equivalent amount of quinine for alprenolol as used in that procedure. In this regard, see also the alprenolol-Sepharose ® gel procedure described in Cherksey et al., *J. Membr. Biol.*, Vol. 84, pp. 105–116 (1985). Similar quinine gels using short-chain polysaccharide or monosaccharide support materials may also be formed.

EXAMPLE 3

Preparation of "Quinine Gel"

A quinine containing gel is produced exactly according to the procedure described by Caron et al., *J. Biol. Chem.* Vol. 254, pp. 2923–2927 (1979), but substituting for alprenolol in the procedure titled "Preparation of Alprenolol Agarose Gel" (page 2926) an equivalent amount of quinine. Thus, about 200 ml of packed agarose (e.g. Sepharose ® 4B) is washed extensively free of sodium azide with water. The moist gel is resuspended in 450 ml of 0.3M NaOH and stirred. 1,4-butanediol diglycidyl ether (0.33 moles, 66 g) is added dropwise and the mixture allowed to stir gently overnight at room temperature. The gel is then washed to neutrality with water. The moist gel is then added to 300 ml of 0.5M sodium phosphate buffer pH 6.3 and 300 ml of 2M $Na_2S_2O_3$. The mixture is stirred for 8 hrs. at room temperature and washed with water until a silver nitrate test is negative to yield the sodium thiosulfate derivatized Sepharose (65–70 ml.) It is suspended in 100 ml of sodium bicarbonate pH 8 containing 40 mg of disodium EDTA. Dithiothreitol, 4 gm, is added and the mixture is stirred for 3 hrs. at 23 degrees C. The activated Sepharose is washed rapidly with 1 liter of water freshly bubbled with nitrogen to remove air.

The addition of the sulfhydryl group of the gel to quinine is accomplished as follows. The beads are mixed with 20 ml of an aqueous solution containing about 0.8 gm of quinine hydrochloride. After stirring at 23 degrees for 20 minutes, the gel is immersed in a 90 degree water bath and 1 ml of aqueous $K_2S_2O_8$ (46 mg/ml) is added every 12 minutes for 2 hours. The quinine derivatized gel is washed extensively in a column with 4 liters of water at 4 degrees, 200–300 ml of 0.1M sodium bicarbonate and finally treated with a 1% solution of $NaBH_4$ in 0.1M sodium bicarbonate/sodium carbonate buffer pH 9 for 3 hours at 4 degrees. The gel is washed extensively with water (4–8 liters) and may be used directly for the isolation of the $K^+/Cl^-$ channel. Alternatively, it may be stored in 0.02% $NaN_3$ until used.

The above furosemide and quinine gels are useful in the isolation and purification of the $K^+/Cl^-$ channel protein and may also be used directly as therapeutic agents. The gels may be administered orally to human or animal subjects to inhibit gastric acid secretion and thus treat or prevent gastric ulcer, to enhance diuresis, to prevent diarrhea, particularly diarrhea associated with cholera, or to treat other membrane transport, cellular volume or cellular pressure disorders. Furthermore, such gels, especially when derived from short-chain saccharides or monosaccharides such as glucose or dextrose, or from dextran, may be applied topically to the eye to reduce intraocular pressure, as for example to treat glaucoma.

The $K^+/Cl^-$ channel protein may be isolated and purified using the furosemide or quinine affinity gels described above following methods well known in the art, as discussed below.

EXAMPLE 4

Purification of Channel Protein

Choroid plexus ventricular cell membranes were obtained and solubilized in 100 mM sodium citrate/3% sodium cholate and purified in one of the two affinity gels. The protein was eluted with excess of drug and dialyzed for 72 hours against 400 mM sucrose/1% cholate. Typically the gels yield 30 μg of purified protein from 0.2 g of cell membrane.

The purified protein was analyzed by gel filtration chromatography (Sepharose® CL-4B) and by SDS-polyacrylamide gel electrophoresis (PAGE). Gel filtrated protein from either gel exhibited the same two sharp peaks at m.w. 420 kD and 810 kD, as shown in FIG. 1. This figure shows the results of chromatography of native vesicles (top), protein purified by the furosemide-gel (F, middle) and quinine-gel (Q, lower). Two peaks are seen in the traces of the purified protein, these being the monomer and the dimer form of the same protein as ascertained by SDS-electrophoresis and by electrical measurements. The protein purified by the quinine gel exhibit the same peaks, and only the same peaks, as the furosemide gel purified protein. This strongly suggests that the same protein is purified by both gels. Elution from the column (1.5×155 cm, i.d.) was at a flow rate of 0.3 ml/min. Fractions of 0.5 ml were collected and protein was determined as the optical absorbance at 280 nm ($A_{280}$).

Protein was subjected to SDS-PAGE under non-reducing conditions in order to break any dimeric associations. Under these condition, only a single band of m.w. 280 kD was found, consistent with the assignment of the peaks (FIG. 1) as a monomer and its associated dimer. Thus, only one single protein was purified. This was further assessed electrophysiologically as the protein from each peak from the Sepharose® was separately reconstituted into lipid bilayers and gave identical results. The differences in molecular weight found using the two methods is expected, as gel filtration typically overestimates the molecular weight. Corrections for bound deoxycholate is estimated as 0.29 mg/mg protein (Conti-Fronconi, et al., *Ann. Rev. Biochem.*, Vol. 51, pp. 491-530 (1982)) and yields a value of 300 kD, well in agreement with the results obtained by SDS-PAGE, which may underestimate by as much as 20% (Eldefrawi, et al., *Ann. N.Y. Acad. Sci.*, Vol. 264, pp. 183-202 (1975)).

EXAMPLE 5

Transport Electrical Properties of Channel Protein

The electric properties of the protein were studied by reconstituting them into planar lipid bilayers (phosphatidylethanolamine/phosphatidylserine=5/1) formed at the tip of a patch clamp pipette (i.d.=1 μm) (Coronado, et al., *Biophys. J.*, Vol. 43, pp. 231-236 (1983)). The potential was maintained at 80 mV under voltage-clamp conditions and the external bath contained 150 mM of either KCl, choline-Cl, NaCl, K-gluconate or K-isethionate. All contained 1 mM $CaCl_2$ and 5 mM TRIS, pH=7.4. Furosemide or quinine could be included. Under these conditions of high $Ca^{++}$ concentration, the currents mediated by the channel protein were discrete, fluctuating less than 0.5 pA. The currents carried by $K^+$ ($I_K$) and $Cl^-$ ($I_{Cl}$) could be described by the Goldmann equation; the findings obtained at a potential difference of 80 mV across the bilayer are summarized in Table I.

TABLE I.

| Currents through reconstituted channel protein | | | |
|---|---|---|---|
| $I_K$(pA) | $I_{Cl}$(pA) | $I_{K,Cl}$(pA) | |
| 100 | 24 ± 9(13) | 90 ± 3(12) | control |
| 93 ± 1(10) | 8.2 ± 1(29) | 101 ± 2(11) | +$10^{-3}$ M furosemide |
| 39 ± 6(14) | 17 ± 4(15) | 44 ± 2(29) | +$10^{-4}$ M quinine |

Note:
The currents were normalized relative to $I_K$, ± S.E.M. (number of reconstitutions).

Different amounts of protein could be reconstituted; the smallest $I_K$ observed was about 1 pA, but extensive reconstitutions resulted in $I_K$ of more than 200 pA. The channel protein had a selectivity of $K^+$ over $Na^+$ or $choline^+$ of at least 10. The selectivity of $Cl^-$ over gluconate was higher than 6. When a flow of $K^+$ and $Cl^-$ was initiated in opposite directions, the flows interacted, since the total current $I_{K,Cl}$ was smaller than the sum of the currents obtained with each ion species alone. This interaction suggests that the fluxes take place in closely associated parts of the same protein. Furosemide reduced $I_{Cl}$ and eliminated the interaction since the sum of $I_K$ and $I_{Cl}$ equaled $I_{K,Cl}$ in this case. The half maximal dose for inhibition of $I_{Cl}$ was about $10^{-6}$ mol. Quinine blocked with a half maximal dose of 70 μM for $I_K$, 450 μM for $I_{Cl}$. The action of the drugs was rapid and reversible, new steady-states in the currents being established in less than two seconds. $I_{K,Cl}$ was reduced by 38%±3 (n=17, SEM) when the $Ca^{++}$ activity in the external bath was reduced from $10^{-7}$ to $10^{-8}$ M and by 45%±3 (n=14, SEM) when pH was reduced from 7.2 to 6.9. The degrees of inhibition should be considered in connection with the fact that the protein was orientated at random in the bilayer. Thus, only half of the inhabitable sites may be exposed to the external bath where pH and $Ca^{++}$ were changed.

The results were similar whether the protein was purified from quinine-gel or the furosemide-gel. Furthermore, the same protein could be purified from bovine kidney cortex, bovine brain cortex, bovine heart muscle, rabbit small intestinal baso-lateral membrane and murine Ehrlich ascites tumor cells. The protein was not observed in human red blood cells or in apical membrane from small intestine or cornea.

The wide distribution and the properties of the channel protein demonstrate its utility as a volume regulator. In the tissues studied, the intracellular $K^+$ and $Cl^-$ activities are above electrochemical equilibrium (Hoffmann, *Biochim. Biophys. Acta*, Vol. 864, pp. 1-21 (1986); Zeuthen et al., *Renal Physiol. Basel*, Vol. 9, p. 91 (1986)). Thus, osmotically-induced changes in intracellular $Ca^{++}$ (Foskett et al., *Am. J. Physiol.*, Vol. 248, pp. C27-C36 (1985)) could control passive volume regulatory fluxes of K+ and Cl− via the protein. Furthermore, the sensitivity of the conductance to quinine and furosemide closely resembles that determined for volume regulation (Grinstein et al., *Am. J. Physiol.*, Vol. 246, pp. C204–C215 (1984)).

In addition, the K+/Cl− channel protein may be used in methods now standard in the art to produce polyclonal or monoclonal antibodies thereto. These antibodies may be used in accord with standard immunofluorescence or radioimmunoassay techniques to produce a diagnostic assay capable of determining, in histopathological samples, the extent to which volume and pressure problems may result from abnormally high or abnormally low presence of the channel protein in appropriate membranes. Alternately, radio-labeled or fluorescent-labelled furosemide ketone adduct (II) may be used to quantitate the presence of the channel protein.

The purified K+/Cl− channel may also be used in conjunction with radio-labeled furosemide or butmetamide (U.S. Pat. No. 3,634,583), or in conjunction with a radio-labeled or fluorescent-labeled furosemide ketone adduct, in a screening procedure capable of evaluating the ability of new chemical entities to displace the above labeled compounds. Entities that displace the bound labeled channel protein blocker may be presumed to affect volume and pressure control mechanisms in humans and other animals and are therefore candidates for further in vivo evaluation. The present K+/Cl− channel protein is thus useful in providing an in vitro assay methodology capable of screening large numbers of test compounds without requiring the use of large numbers of experimental animals. The methods to be employed in such screening assays are well known to those skilled in the art given the present disclosure.

What is claimed is:

1. A purified K+/Cl− channel protein capable of binding both furosemide and quinine.

2. A K+/Cl− channel protein produced by extracting said channel protein from cell membrane material by extraction with an affinity gel, said affinity gel comprising a channel protein binding compound covalently bonded to a polysaccharide or monosaccharide support material.

3. The channel protein of claim 2 wherein said channel protein binding compound comprises furosemide, quinine, or a derivative of furosemide or quinine.

4. The channel protein of claim 3 wherein said channel protein binding compound is a furosemide derivative and said furosemide derivative is a methylvinyl ketone adduct of furosemide having the formula

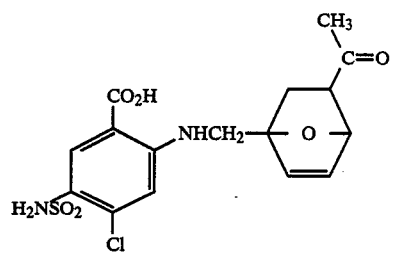

5. The channel protein of claim 3 wherein said affinity gel is a quinine affinity gel.

6. A method of screening a chemical entity for activity in modulating membrane transport, cellular volume or cellular pressure, said method including the step of measuring the ability of said chemical entity to bind to the channel protein of claim 1.

7. A method of screening a chemical entity for activity in modulating membrane transport, cellular volume or cellular pressure, said method including the step of measuring the ability of said chemical entity to displace a channel protein binding compound bound to the channel protein of claim 1.

8. The method of claim 7 wherein said channel protein binding compound is selected from the group consisting of furosemide, quinine, butmetamide, derivatives of furosemide, quinine and butmetamide, and radiolabeled and fluorescent-labeled derivatives of the foregoing compounds.

9. A method of extracting a K+/Cl− channel protein from cell membrane material comprising the step of extracting with an affinity gel, said affinity gel comprising a channel protein binding compound covalently bonded to a polysaccharide or monosaccharide support material.

10. The method of claim 9 wherein said channel protein binding compound comprises furosemide, quinine, or a derivative of furosemide or quinine.

11. The method of claim 10 wherein said channel protein binding compound is a methylvinyl ketone adduct of furosemide.

12. The process of claim 10 wherein said affinity gel is a quinine affinity gel.

* * * * *